United States Patent
Neuwirth

[11] Patent Number: 6,162,166
[45] Date of Patent: Dec. 19, 2000

[54] APPARATUS FOR PRODUCING ALTERNATING MAGNETIC FIELDS FOR INDUCING EDDY CURRENTS IN AN ORGANISM

[76] Inventor: Gerald Neuwirth, Ponauer Str. 35/VI/3, Spittal/Drau 9800, Austria

[21] Appl. No.: 09/271,360

[22] Filed: Mar. 17, 1999

Related U.S. Application Data

[63] Continuation of application No. PCT/AT98/00129, May 18, 1998.

[30] Foreign Application Priority Data

Jul. 22, 1997 [AT] Austria .................................. 458/97 U

[51] Int. Cl.$^7$ ........................................................ A61N 1/00
[52] U.S. Cl. .................................................................. 600/14
[58] Field of Search ............................................ 600/9–15

[56] References Cited

U.S. PATENT DOCUMENTS

| | | | |
|---|---|---|---|
| 3,678,337 | 7/1972 | Grauvogel ................................... | 317/4 |
| 4,095,588 | 6/1978 | Goldman et al. ........................... | 600/9 |
| 4,315,503 | 2/1982 | Ryaby et al. ............................... | 600/9 |
| 4,993,413 | 2/1991 | McLeod et al. ........................... | 600/13 |
| 5,169,380 | 12/1992 | Brennan ..................................... | 600/14 |
| 5,344,384 | 9/1994 | Ostrow et al. ............................. | 600/13 |
| 5,842,966 | 12/1998 | Markoll ..................................... | 600/14 |

FOREIGN PATENT DOCUMENTS

| | | |
|---|---|---|
| 0084019 | 7/1983 | European Pat. Off. . |
| 0392626 | 10/1990 | European Pat. Off. . |
| 0459401 | 12/1991 | European Pat. Off. . |
| 3721864 | 1/1989 | Germany . |

*Primary Examiner*—Samuel G. Gilbert
*Attorney, Agent, or Firm*—Jacobson, Price, Holman & Stern, PLLC

[57] ABSTRACT

In an apparatus for producing alternating magnetic fields for inducing eddy currents in an organism, wherein the apparatus (1) is designed to produce and deliver alternating magnetic fields of an adjustable, low frequency at pulses having steep pulse edges with harmonic wave portions, it is provided that the magnetic field strength of the alternating magnetic fields delivered by the apparatus (1) is chosen to be smaller than 300 A/m and, in particular, between 100 and 250 A/m, preferably in an adjustable manner, in order to induce eddy currents in an organisms by such alternating magnetic fields by way of a simple system, for instance, for treating ear noises, tinnitus or the like.

15 Claims, 2 Drawing Sheets

APPARATUS FOR PRODUCING ALTERNATING MAGNETIC FIELDS FOR INDUCING EDDY CURRENTS IN AN ORGANISM

This is a Continuation Application based on PCT/AT98/00129, filed May 18, 1998.

BACKGROUND OF THE INVENTION

The present invention relates to an apparatus for producing alternating magnetic fields for inducing eddy currents in an organism as well as the use of such an apparatus, wherein the apparatus is designed to produce and deliver alternating magnetic fields of an adjustable, low frequency at pulses having steep pulse edges with harmonic wave portions.

Various apparatus for producing and delivering alternating electromagnetic waves for treating and examining organisms are known, wherein it is to be generally anticipated that the depth of penetration of such alternating electromagnetic fields is a function of the frequency. An apparatus of the initially defined kind has become known, for instance, from EP-A 0 084 019. In general, the electric field may be neglected as long as the frequency is within a very low range, i.e., in the range of what is called an extremely low frequency. By contrast, an alternating magnetic field induces eddy currents in the whole organism, which result in charge transfers in the cell membranes, thereby provoking stimulations of the vegetative nervous system capable of, for instance, reducing blockages present in the organism.

SUMMARY OF THE INVENTION

The present invention aims at providing an apparatus for producing alternating magnetic fields for inducing eddy currents in an organisms, which enables the concerted and dangerless production of eddy currents in an organism in a structurally simple manner so as to cause the purposeful influence of potential charge transfers in the cell membranes and eliminate or relax existing blockages by aid of the thus induced stimulation of the vegetative nervous system. To solve these objects, the apparatus according to the invention essentially is characterized in that the magnetic field strength of the alternating magnetic fields delivered by the apparatus is chosen to be smaller than 300 A/m and, in particular, between 100 and 250 A/m, preferably in an adjustable manner. Since alternating magnetic fields of an adjustable, low frequency are delivered by the apparatus according to the invention, simple adaptation to the varying sensitivities of different organisms is feasible, it having been found that the sensitivity is maximal at the frequency that corresponds with the EEG α rhythm of the person to be treated. The low field strengths selected according to the invention, moreover, ensure that the desired effects with a view to inducing eddy currents in an organism are achieved by problem-free and absolutely dangerless handling. Pulses are produced and delivered in the form of waves having pulsating steep edges with harmonic wave portions, wherein the pulses inherent in an organism are incited and assisted to the optimum degree by such induced pulses delivered to the organism, if the frequency of the alternating magnetic field externally applied is synchronous with the pulses inherent in the organism, thereby assisting in the vegetative nervous system stimulations sought.

A particularly simple embodiment of the invention easy to produce in terms of construction preferably is designed such that the apparatus comprises an astable multivibrator including at least one transistor and at least one bipolar iron core coil for delivering the alternating fields. It is thereby feasible in a relatively simple and cost-effective manner by means of elements known per se to produce and deliver the alternating magnetic fields at pulses having steep wave edges with harmonic wave portions.

An apparatus according to the invention is applicable, in particular, for the treatment of ear noises or tinnitus, sleep disturbances, headaches, migraine, cervical vertebral and spinal vertebral syndromes, nervousness and circulatory disturbances, wherein it has been generally shown that beneficially acting ranges of the alternating magnetic fields with an adjustable, low frequency are chosen such that the frequency lies below 20 Hz and, in particular, between 3 and 15 Hz, as in correspondence with a further preferred embodiment of the apparatus according to the invention. In general, a subdivision into substantially two treatment specific ranges has been found, a frequency range of between 3 and 6 Hz generally having sedative and anti-spasmodic effects. By contrast, the effects of the frequencies ranging between 8 and 15 Hz substantially are stimulating, pain-relieving and stabilizing. Furthermore, it may be anticipated that frequencies of below 8 Hz substantially induce hemangiectases, whereas frequencies of above 12 Hz generally lead to contractions of the blood vessels, wherein the high frequency range indicated above should be applied only if low frequencies are without effect.

In order to further enhance the adapation to the desired effect, of the frequency to be adjusted, it is contemplated according to another preferred embodiment that wobbling and, in particular, digital wobbling of the frequency by±25% and, preferably,+10% is provided.

In order to ensure a structurally simple construction and, in particular, provide for apparatus that can be operated independently of a mains supply, it is moreover suggested according to a further preferred embodiment that a low voltage d.c. source, in particular a 9 volt d.c. voltage source, is provided as a power supply. In that manner, also movable and portable apparatus independent of the mains supply may be constructed in a simple manner by providing a battery as the d.c. voltage supply, which is of particular advantage when applied in the treatment of tinnitus.

As already indicated above, the apparatus according to the invention may be employed for treating a plurality of applications, wherein it is suggested according to another preferred embodiment, in particular for treating ear noises or tinnitus, that the apparatus is integrated in a headphone with one bipolar iron core coil each being contained in each of the microphones of the headphone. Optionally, a configuration comprising but one bipolar iron core coil is conceivable, for instance, if ear noises occur in one ear only. In doing so, an apparatus according to the invention may be readily realized in such a headphone, optionally with an accordingly small-structure auxiliary implement, so that a construction easy to apply and use is altogether achievable.

As already indicated above, an essential feature of the apparatus according to the invention resides in the availability of adjustable, low frequencies for the treatment of various indications as well as for obtaining the optimum harmonization possible, between the alternating magnetic fields and the pulses inherent in the person to be treated. In this context, it is proposed according to a further preferred embodiment that the apparatus comprises a plurality of switches or selection means for adjusting a desired frequency. This renders feasible in a simple manner the adaptation to desired frequency ranges as well as the achievement of as precise an agreement as possible with the frequency of the pulses inherent in the person to be treated.

In order to further facilitate the handling and monitoring of the apparatus according to the invention, it is, furthermore, provided in a preferred manner that the apparatus comprises at least one display and, in particular, an LCD display. In order to further automatize the use of the apparatus according to the invention, it is proposed that the apparatus comprises a timer, as in correspondence with a further preferred embodiment of the invention.

BRIEF DESCRIPTION OF THE DRAWINGS

In the following, the invention will be explained in more detail by way of exemplary embodiments schematically illustrated in the accompanying drawing. Therein.

DETAILED DESCRIPTION OF PREFERRED EMBODIMENTS OF THE INVENTION

Figure 1:
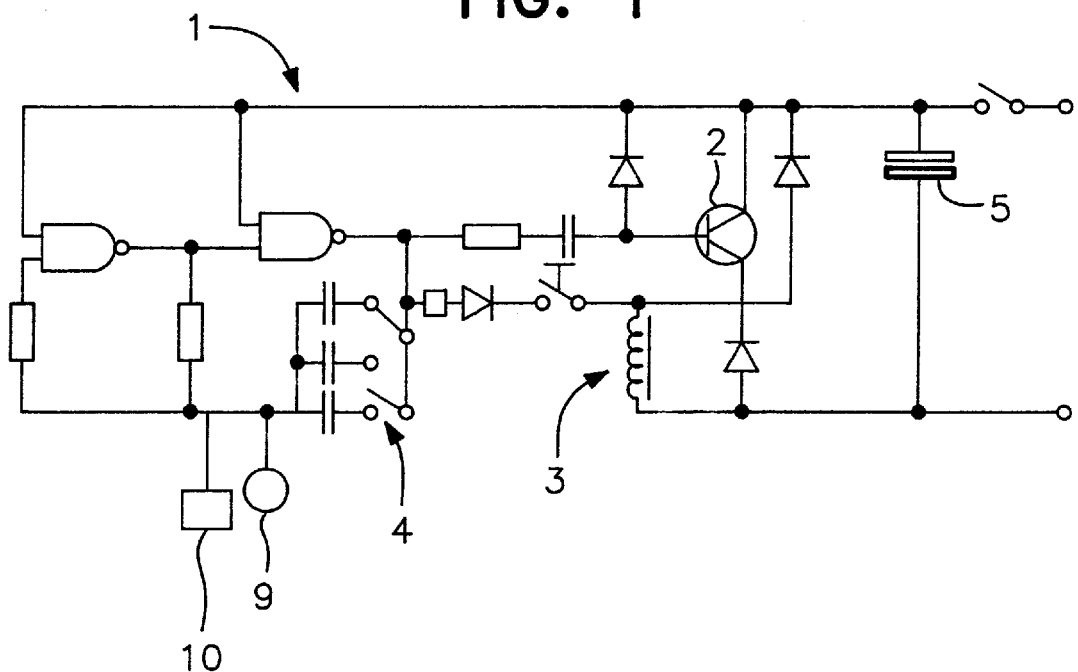
FIG. 1 is a schematic circuit diagram of an apparatus according to the invention.
Figure 2:
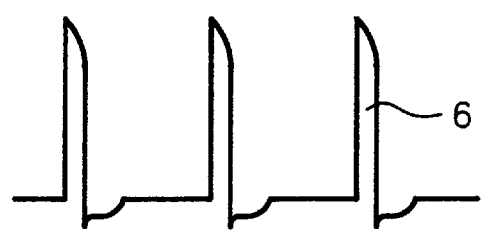
FIG. 2 is a graphical representation of the low frequency pulses produced by the apparatus according to the invention and having pulsating steep edges with harmonic wave portions.

FIG. 1 schematically illustrates the circuit of an astable multivibrator 1 with a transistor being denoted by 2 and a bipolar iron core coil being generally denoted by 3. In addition, a plurality of switches or selection elements 4 and a d.c. voltage source 5 are indicated. The astable multivibrator depicted in FIG. 1 serves to produce steep harmonic-wave-like pulses 6, as is schematically indicated in FIG. 2. The waves with pulsating steep edges, of the pulses 6 are achieved by harmonic wave portions up to the GHz-range. In addition, at least one display is indicated by 9, while 10 schematically denotes an integrated or coupleable timer.

In order to produce the steep harmonic-wave-like pulses 6 schematically illustrated in FIG. 2, the transistor 2 conducts and blocks in the rhythm of the selected frequency, wherein the pulsed collector current of the transistor 2 accordingly magnetizes the core of the iron core coil 3. The magnetic field strength in that case may be chosen below 300 A/m and, in particular, between 100 and 250 A/m.

By means of the three switches 4 indicated in the schematic circuit diagram of FIG. 1, the frequencies listed below may be achieved by combining the switches, the left-hand column of the following Table each indicating the switches to be actuated for obtaining the frequencies indicated in the right-hand column.

| Switch | Hz |
| --- | --- |
| 1 | 4,5 |
| 2 | 9,5 |
| 3 | 15 |
| 1 and 2 | 3 |
| 1 and 3 | 3,5 |
| 2 and 3 | 6 |
| 1 and 2 and 3 | 2,5 |

Alternatively to a switch arrangement as illustrated in FIG. 1, which comprises three switches or selection elements, a frequency of 5 or 10 Hz, respectively, may, for instance, be adjustable in a simple embodiment by providing but one switch.

Figure 3:
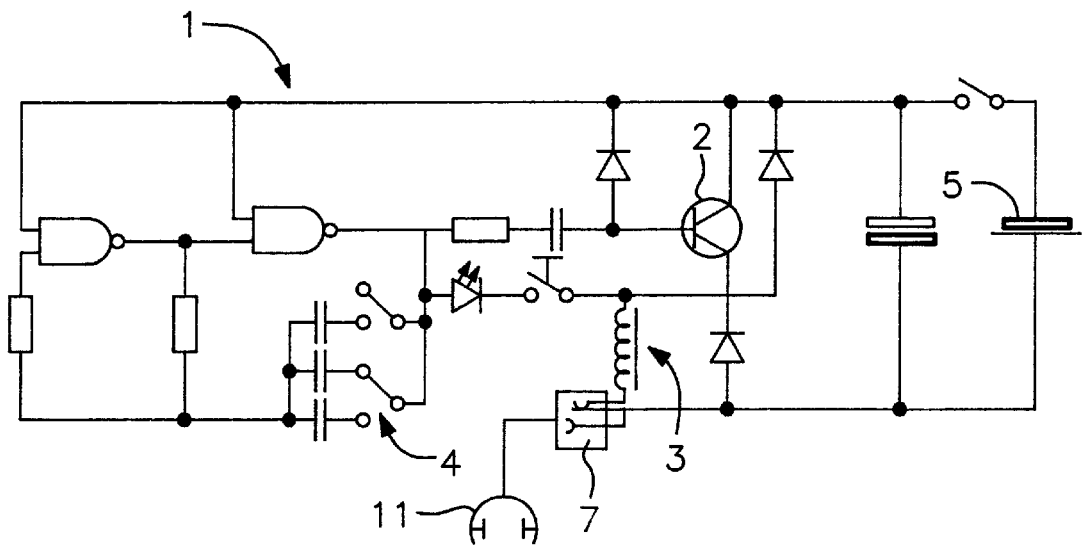
FIG. 3 is a modification of the circuit diagram of FIG. 1 to be used in a portable apparatus.

FIG. 3 is a modification or further development of the schematic circuit of the astable multivibrator 1 of FIG. 1, in which the reference numerals of FIG. 1 have been retained for identical elements. The schematic circuit according to FIG. 3 is intended, in particular, for a portable apparatus to be used for treating tinnitus. The arrangement of the switching or selection means 4 is devised so as to be able to choose among four different frequencies. In the circuit according to FIG. 3, a battery is used as the d.c. voltage source 5. By means of the astable multivibrator represented in FIG. 3, steep harmonic-wave-like pulses 6 are produced as they are produced in FIG. 1 and schematically indicated in FIG. 2, wherein a socket 7 for connecting an external headphone in order to transmit these pulses to a headphone is indicated in FIG. 3. As already pointed out above, such an apparatus may be integrated in a headphone, in particular for treating ear noises, one bipolar iron core coil 3 each being provided in each headphone for that purpose.

Figure 4:
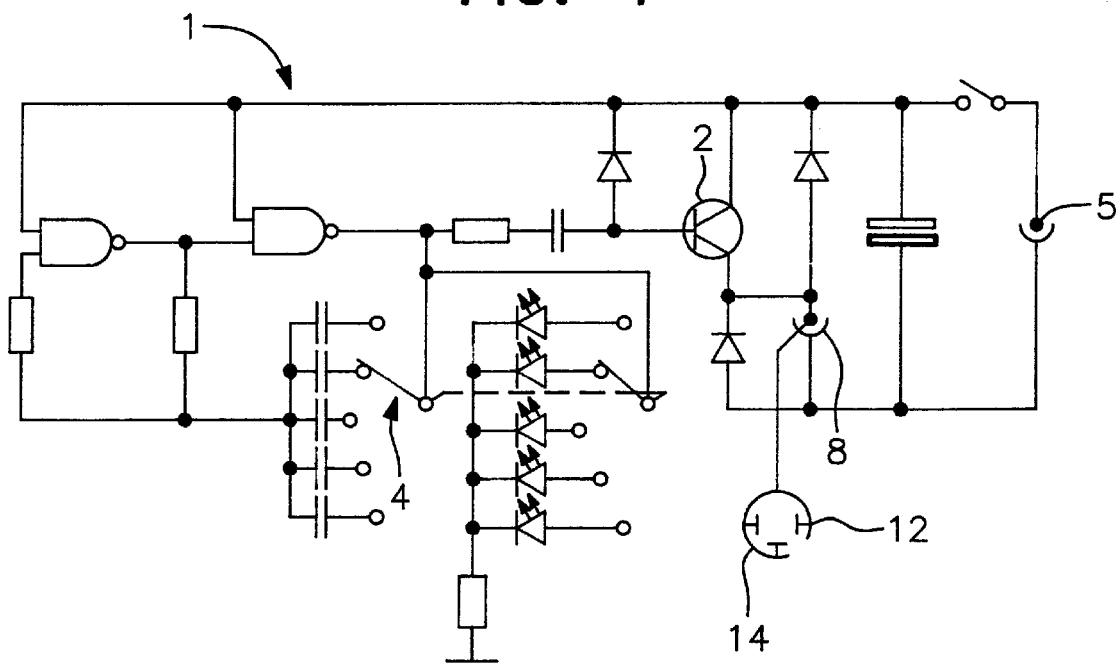
FIG. 4 is a further circuit arrangement of the apparatus according to the invention to be used as a stationary apparatus.

The schematic circuit arrangement according to FIG. 4, which is a further development of the circuit arrangement depicted in FIGS. 1 and 3, is devised such that five switches or selection elements 4 are employed. The five switches 4 indicated in the schematic connection chart of FIG. 4 allow for the achievement of the frequencies listed below, the left-hand column of the following Table each indicating the switches to be actuated for obtaining the frequencies listed in the right-hand column.

| Switch | Hz |
| --- | --- |
| 1 | 3 |
| 2 | 4,5 |
| 3 | 6 |
| 4 | 9,5 |
| 5 | 15 |

In the circuit arrangement according to FIG. 4, no bipolar iron core coil 3 is indicated, these being arranged in headphones to be carried externally, which are not illustrated. The headphones are plugged into the socket 8 and the iron core coils are incited in the manner described above.

Advantageously, the circuit arrangement according to FIG. 4 may be incorporated in a stationary apparatus such that the schematically illustrated d.c. voltage source 5 may be designed as a socket for a main power unit of, for instance, 9 volts in order to adapt the apparatus for a long-duration use.

In addition to the configuration in the form of a headphone, it may alternately be provided to carry such an apparatus for producing alternating magnetic fields for inducing eddy currents in an organism as a mobile apparatus directly on the body, for instance in a jacket pocket or in a bag to be carried on the body. Alternately, it may be provided to integrate the apparatus in a pillow for the head or a similar element, which, for instance, in the lying position is arranged in the neck region, particularly for treating headaches or cervical vertebral and spinal vertebral syndromes.

What is claimed is:

1. An apparatus for producing alternating magnetic fields for inducing eddy currents in an organism, said apparatus comprising:

means for producing alternating magnetic fields of an adjustable, low frequency;

means for producing pulses having steep pulse edges with harmonic wave portions by conducting and blocking selected ones of said adjustable low frequency and, said means for conducting and blocking having means for receiving said pulses;

at least one bipolar iron core coil receiving the pulses and producing a magnetic field strength from said alternating magnetic field in a range of 100 A/m to 300 A/m; and wherein the apparatus is integrated in a headphone, said headphone having at least one microphone, and said bipolar iron core coil being contained in the microphone of the headphone.

2. An apparatus according to claim 1, wherein the means for producing alternating magnetic fields includes an astable multivibrator including at least one transistor and said at least one bipolar iron core coil for delivering the alternating magnetic fields.

3. An apparatus according to claim 1, wherein the apparatus further comprises means for selecting said frequency and said frequency is below 20 Hz.

4. An apparatus according to claim 1, wherein said apparatus further comprising:

means for providing wobbling of said frequency.

5. An apparatus according to claim 1, wherein said apparatus further comprising:

a power supply for providing a low d.c. voltage source, said source being a nine volt d.c. voltage source.

6. An apparatus according to claim 1 wherein the apparatus comprises a plurality of switches for adjusting a desired frequency of said adjustable, low frequency.

7. An apparatus according to claim 1 wherein the apparatus comprises at least one display.

8. An apparatus according to claim 1, wherein the apparatus comprises a timer.

9. The apparatus according to claim 1, wherein said apparatus comprises means for treating ailments selected from the group consisting of ear noises, sleep disturbances, headaches, migraine, cervical vertebral and spinal vertebral syndromes, nervousness and circulatory disturbances.

10. An apparatus according to claim 1, wherein the apparatus further comprises means for selecting said frequency and said frequency is between 3 and 15 Hz.

11. An apparatus according to claim 1, wherein said apparatus further comprising:

means for providing digital wobbling of said frequency.

12. An apparatus according to claim 1, wherein said apparatus further comprising:

means for providing wobbling of said frequency by+/− 25%.

13. An apparatus according to claim 1, wherein said apparatus further comprising:

means for providing wobbling of said frequency by+/− 10%.

14. An apparatus according to claim 1, wherein the apparatus comprises a plurality of selection means for adjusting a desired frequency of said adjustable, low frequency.

15. An apparatus according to claim 1, wherein the apparatus comprises at least one LCD display.

* * * * *